United States Patent [19]

Nose et al.

[11] 4,311,587
[45] Jan. 19, 1982

[54] FILTER ARRANGEMENT DENYING BACTERIA ENTRY TO PERITONEUM

[75] Inventors: Yukihiko Nose, Cleveland Heights; Paul S. Malchesky, Painesville Township, Lake County, both of Ohio

[73] Assignee: Japan Foundation for Artificial Organs, Cleveland, Ohio

[21] Appl. No.: 102,140

[22] Filed: Dec. 10, 1979

[51] Int. Cl.³ .................... A61M 5/00; B01D 31/00
[52] U.S. Cl. .................... 210/136; 128/213 A; 210/651
[58] Field of Search ................ 210/22 A, 321 A, 136, 210/134, 321 B, 651; 128/213 A

[56] References Cited

U.S. PATENT DOCUMENTS 3,545,438 12/1970 DeVries .................... 128/213 A
3,825,493 7/1974 Brown et al. ............. 128/213 A X
3,864,259 2/1975 Newhart .................... 210/136 X
4,021,353 5/1977 Raines et al. .............. 128/214 R X

FOREIGN PATENT DOCUMENTS 2734248 8/1979 Fed. Rep. of Germany ... 128/213 A

OTHER PUBLICATIONS

Stephen et al., "Recirculating Peritoneal Dialysis with Subcutaneous Catheter," from TASIAO, vol. XXIII, 1976, pp. 575-579.

Primary Examiner—Frank A. Spear, Jr.
Attorney, Agent, or Firm—Baldwin, Egan, Walling & Fetzer

[57] ABSTRACT

A filter connection for peritoneal dialysis is presented including, in a flow line from a source of fresh dialysate solution carried on the patient's body, and under pressure, through a bacteria filter of sub-micron porosity for removing microorganisms generally greater than about 0.2 microns (nominal size) together with tubular connections leading from the filter toward a catheter inserted in the patient's peritoneum including in order from the filter, a first check valve permitting flow only away from the filter, then an outflow port with check valve permitting used dialysis flow only away from the patient, and finally the connection to the catheter tube.

3 Claims, 8 Drawing Figures

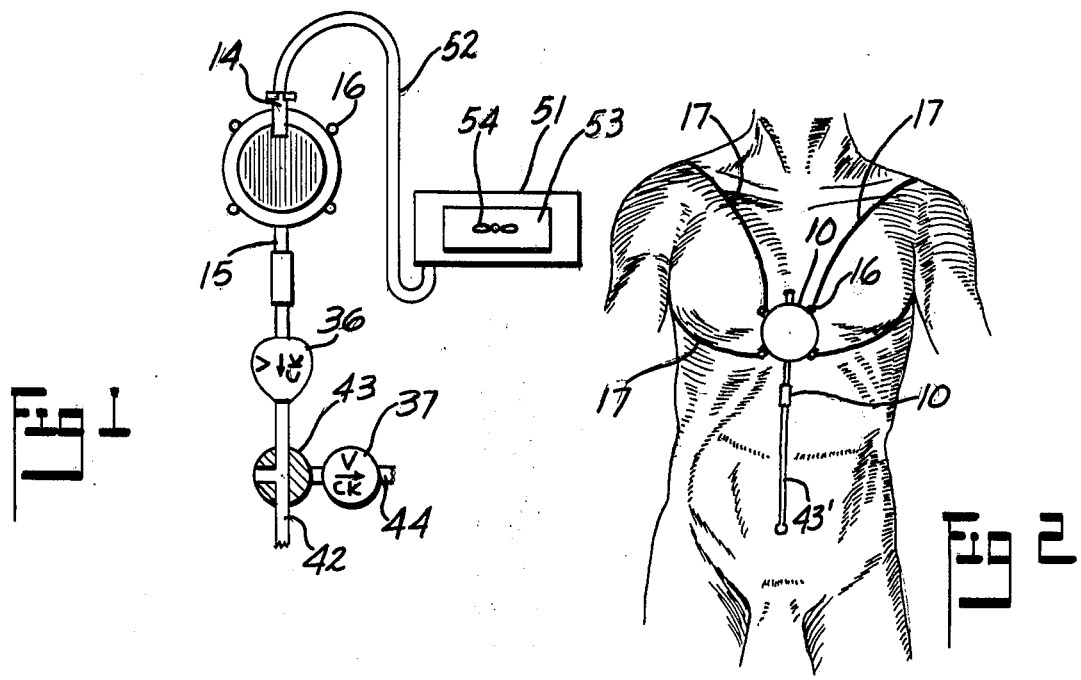
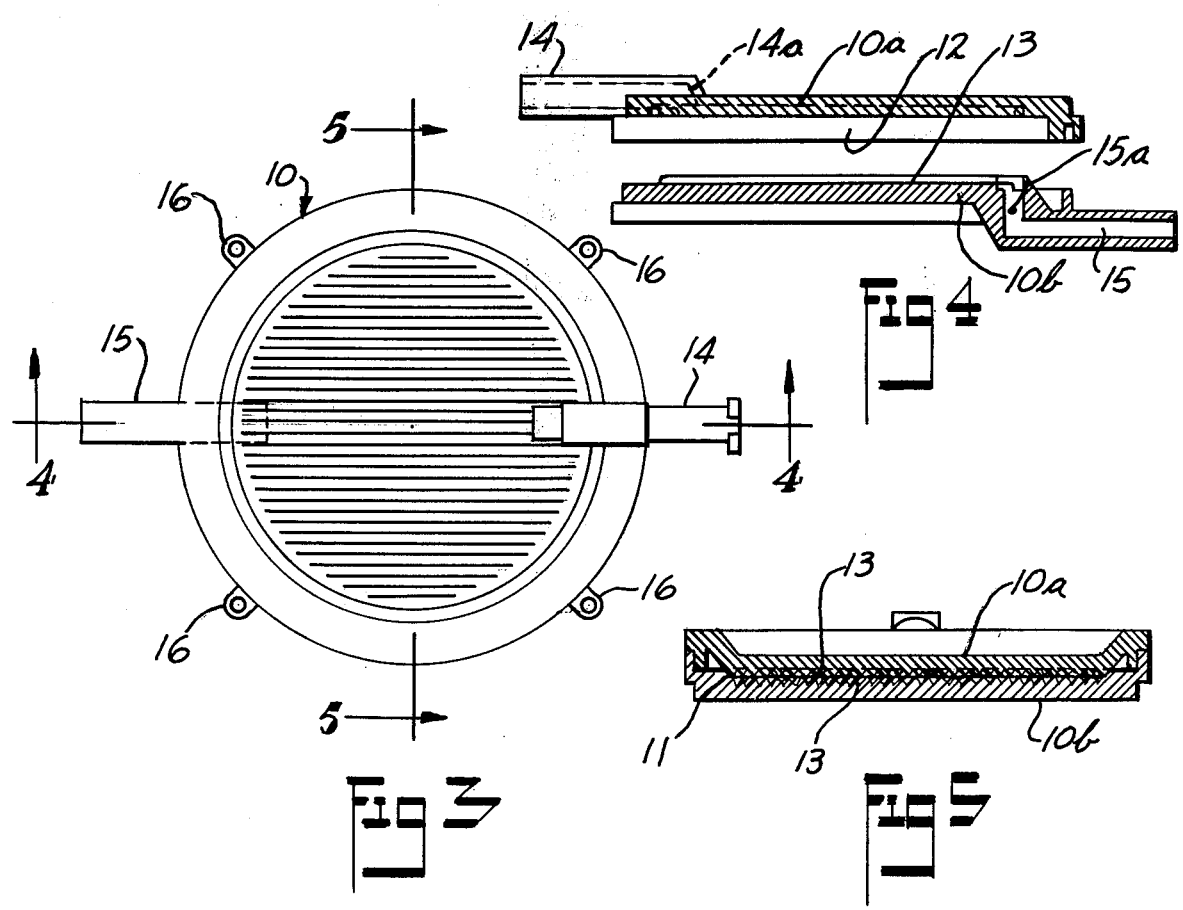

FILTER ARRANGEMENT DENYING BACTERIA ENTRY TO PERITONEUM

FIELD OF THE INVENTION

This invention presents an arrangement for peritoneal dialysis in treatment for chronic renal failure.

PRIOR ART

A major deterrent to the widespread acceptance by physicians and the use of peritoneal dialysis for some patients has been the risk or occurrence of peritonitis. Many investigators believe that the basic methodology of carrying out peritoneal dialysis, using one or two liter bottles or bags of fresh dialysate solution and requiring multiple connections to be made during the course of the dialysis, is the major cause of the high incidence of peritonitis. It has been shown, as long ago as 1963, that by using 40-liter glass carboys with the enforcement of strict antiseptic procedures during catheter insertion and dialysis a dramatic decline in peritonitis can be achieved. However, the production of bulk sterile dialysate has not been shown to be practical for large scale application particularly for home dialysis. The introduction of proportioning equipment led to the development of automated machines for the on-line production of dialysate solution. These machines have proved to be quite safe and reliable and the incidences of infection remain generally low. Present portioning machines utilize sterile concentrates and water processed by reverse osmosis.

While the machines have made a major impact in peritoneal dialysis therapy, peritoneal dialysis treatment times are still lengthy. It would appear that for peritoneal dialysis to become a major treatment methodology for chronic renal failure it must be performed continuously as in done through CAPD (continuous ambulatory peritoneal dialysis). CAPD offers continuous peritoneal dialysis and more than fulfills the time requirement (30–40 hrs/wk) while still allowing the patient some off time. CAPD must be done in the absence of a machine and multiple bottles or bags of peritoneal dialysate must be infused daily. While progress is being made to reduce the number of bags required per infusion (by producing bags with the volume requirement per infusion), the requirement of multiple infusions per day still necessitates that multiple connections of bags to the peritoneal catheter be made.

It has been shown that the onset of peritonitis is related to the training of the medical personnel in sterile technique. For example, when tubing changes were carried out by a nurse the occurrence of peritonitis was less than occurred using less well trained personnel. It is apparent from this and other studies that for CAPD, with its multiple advantages, to have an impact in treatment of chronic renal failure the problem of peritonitis must be solved. To solve this problem advances in the delivery system for the peritoneal dialysate must be made. It must be assumed that some bacterial invasion or contamination can occur, therefore, the approach to the problem would be to prevent the contaminants from entering the peritoneal cavity. Based upon this rationale, the inclusion of a sub-micron filter on-line with the fresh dialysate would be most beneficial in preventing peritoneal contamination. Such a filter in combination with an improved fluid processing track, with additional one-way valve or valves, could provide the most practical scheme for preventing bacterial invasion via the dialysate solution.

Millipore Corporation of Bedford, Mass. has been offering a system composed of a fresh dialysate solution supply on an IV pole, a tube leading from the supply to a filter unit containing a 0.22 $\mu$m pore size Millipore membrane, then to a clamp, then through a Y tube connection and through another clamp to a peritoneal catheter and to the abdomen of a patient lying in bed. The third connection of the Y has a tube leading through a clamp to a drainage bottle at a lower level. Applicants' have a similar structure except that the filter is very light and carried on the body of the wearer, and the fresh dialysate solution is in a container carried on the body of the wearer and the dialysate solution is capable of being pressurized. This makes the treatment entirely perambulatory.

SUMMARY OF THE INVENTION

The major features of this invention include a wearable filter for stopping sub-micron particles or bacteria usually greater than about 0.2 microns with (1) an arrangement to attach the source of fresh dialysate solution at the inlet end of the filter, this solution carried in a container carried on the body of the wearer and the solution is capable of being pressurized; (2) the inclusion of a check valve for unidirectional flow of the dialysate solution from the filter toward a peritoneal catheter; (3) a side arm outflow port on the downstream side of the check valve for drainage of the spent dialysate from the peritoneal catheter. Preferably the side arm outflow port may also include a unidirectional valve to prevent backflow of fluid from the outside.

Fluid flow is from the fresh dialysate container through the filter, then through a first check valve and through a side arm connection to the catheter and into the peritoneal cavity. Fluid removal from the peritoneal cavity is by gravity using a drainage bottle held at a lower level and sucking the used solution from the catheter and then through a second check valve and out the side arm. No dialysate from the peritoneal cavity will go through the filter, but is removed through the side arm which usually incorporates a one-way check valve. This directional flow permits the passage of the protein containing peritoneal dialysate to the patient without the plugging up of the filter. The filter valve assembly can be replaced after several times or days of use, using sterile techniques.

Incorporation of a filter may alone not be sufficient. In order to avoid any backflow and direct the proper flow of peritoneal dialysate, one-way valve at the drainage circuit which will be below the previously named one-way valve is preferable. These additional two valves will guarantee the proper function of the filter and eliminate effectively the possible infection of the peritoneal cavity in the continuous peritoneal dialysis procedure.

FIG. 1 depicts the filter schematically with the connections taught by this invention. The major features of this filter with its connections are: (1) a connection point for fresh dialysate solution in a flexible bag carried by the wearer at the intake side of the filter; (2) the use of a sub-micron filter media, to stop bacteria greater than 0.45 $\mu$m and generally about 0.2 $\mu$m; (3) the inclusion of a check valve for unidirectional flow of the fresh dialysate solution into the peritoneal catheter; and (4) side arm outflow port for drainage of the used dialysate from the peritoneal catheter. Preferably the side arm outflow port may also include a unidirectional valve to prevent backflow of fluid from the outside.

All infusion connections are made ahead of the filter so even if contamination does occur the filter may reject it. To be practical the filter must be lengthwise, conform to the body and be lightweight and be held in place on the body of the wearer. Therefore, a flat design of a filter made of plastic, with the ability to secure it in place (such as by straps) would meet these criteria. A stylized drawing of the filter and catheter attached to a patient's body is shown in FIG. 2. Standard filter media: flat sheet, tubular, and hollow fiber as well as basic valve designs exist for this purpose.

A preliminary study of an in-line bacterial filter was carried out. To keep the filter design simple and low in cost minimal membrane area should be employed, which requires a consideration of the pressure and time required to infuse the fluid.

A preliminary study on 47 mm diameter (17.35 cm$^2$) Millipore sub-micron (0.45 and 0.22 $\mu$m) particle filters indicates that to deliver sterile IV solution (5% dextrose) flow rate is directly proportional to the applied pressure. At the fluid height of one meter (simulating the situation of a fresh dialysate solution container hung from an intravenous or IV pole) perfusion of two liters of solution through the 0.22 $\mu$m filter would require over one hour, not a practical infusion time. At an applied pressure of 300 mmHg the calculated flow of two liters of the solution through a 35 cm$^2$, 0.22 $\mu$m Millipore filter would take 10 minutes, which is a reasonable infusion time. As applied pressure would be required for the infusion of the solution in a reasonable time with a minimum of membrane area required (consideration may also be given to providing a back-up filter) a specialized jacket or vest is provided for carrying the IV solution and pressuring the bag thereby eliminating the need for an IV pole. This feature should appeal to the patient. In pressuring the fluid for delivery to the peritoneal cavity the majority of the pressure drop occurs across the filter. However, by this methodology it is possible to deliver fluid at pressures higher than those encountered under normal gravity feed from an IV pole. This may be used effectively in opening a catheter that may become plugged.

BRIEF DESCRIPTION OF THE DRAWINGS

FIG. 1 is an elevational view of the essential features of this invention including a sub-micron wearable filter with a place to attach the fresh dialysate solution under pressure to the inlet end of the filter, a tubular connection leading to a check valve and then to a three-way valve providing side arm outflow port with a check valve allowing flow only to discharge, and finally to the catheter for insert into the patient's peritoneum.

FIG. 2 shows the complex of FIG. 1, minus the fresh dialysate solution bag, mounted on the body of a patient with the apparatus in use.

FIG. 3 is one type of sub-micron filter for use in this invention.

FIG. 4 is a sectional view taken along the line 4—4 of FIG. 3 and showing two halves of the filter in a separated position.

FIG. 8 is an elevational view of one form of check valve which may be used in this invention.

DESCRIPTION OF THE PREFERRED EMBODIMENTS

Figure 5:
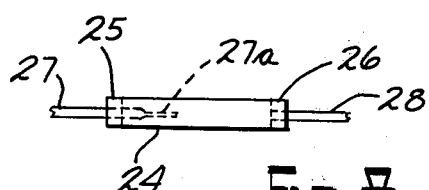
FIG. 5 is a sectional view taken along the line 5—5 of FIG. 3 showing the structure of the filter at right angles to FIG. 4.

FIGS. 1 through 5 show one form of sub-micron filter media which may be used in this invention. This is a known type of filter 10 composed of an upper half 10a of a housing together with a lower half 10b of the housing which, when put together as shown in FIG. 5, has a porous membrane 11 held between a series of sharp ridges 12 on housing portion 10a and another series of sharp ridges on the half 10b of the housing. The flow through this filter is from the inlet end at 14 from a supply of fresh dialysate solution and through a passageway 14a in communication with the upper sides of the valleys between the ridges 12, then through the permeable membrane 11, and then along the valleys between the ridges 13 to a passageway 15a communicating with the outlet tube 15.

The filter has outstanding tabs 16 which may be used as shown in FIG. 2 to attach straps 17 which pass around the body of the patient to hold the equipment in place while the same is in use.

Figure 6:
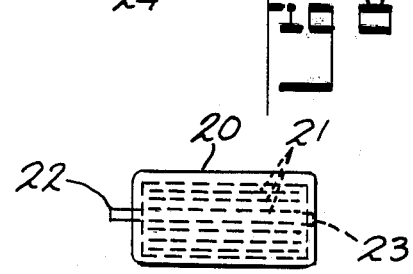
FIGS. 6 and 7 are respectively plan and side elevational views of another known sub-micron filter useful in this invention.
Figure 7:
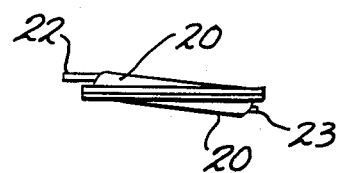

Another type of filter which may be used in this invention is shown in FIGS. 6 and 7. Here a housing 20 holds a membrane of hydrophilic Acropor having a plurality of parallel longitudinally extending ribs 21, supported on an internal nylon support, has fresh dialysate connected at 22, on one side of the membrane and filtered dialysate discharged from the other of the membrane at 23. This filter is made by Gelman Sciences of Ann Arbor, Mich., and is their type AN200, rated at 0.2 microns.

In the sub-micron bacterial filter used in this invention, the membranes 11 and 21 are so chosen that they will capture anything in the dialysate solution greater than about 0.2 microns.

Referring to FIG. 1, the tube connection 15 leads from the filter 10 downwardly to a check valve 36 which permits flow away from the filter only. Then the tube leads through a three-way valve 43 which in the position shown in the drawings connects to the tube 42 which leads to the catheter connection 43' going into the body of the patient. When used dialysate is to be removed from the body of the patient, then the three-way valve 43 is turned counterclockwise 90 degrees to connect with the discharge tube 44 in which line is inserted a check valve 37 allowing fluid passageway only through lines 42 and 44 to discharge.

It will be noted that all types of filter shown herein for use in this invention are of a rather flat construction as seen in FIGS. 5 and 7. That is, the filter is wider than it is thick. Also, preferably, the filters are made chiefly of plastic material to reduce the weight thereof. To be practical, the filter must be lightweight, conformed to the body of the patient, and be held in place. Therefore, the invention uses a plastic design of filter with the ability to be secured to the wearer, such as by straps 17.

Figure 2A:
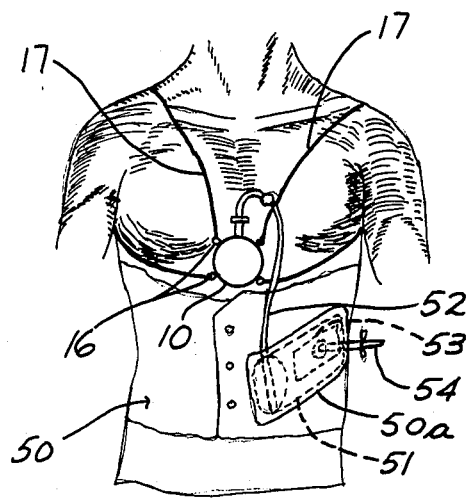
FIG. 2A is like FIG. 2 except that it adds a fresh dialysate solution bag mounted on the wearer and arranged to pressurize the bag.

A specialized jacket or vest 50, seen in FIG. 2A may be worn by the patient for carrying the dialysate solution. The fresh dialysate solution is carried in a flexible bag 51 in a pocket 50a in the vest. It is connected by tube 52 to the intake 14 of the filter 10. Pressure may be applied to bag 51 either by the hand of the wearer, or by a pressure plate 53 having a screw 54 connected to apply pressure to the bag.

In FIG. 8, there is shown a possible structure of a check valve which may be used at 36 or 37 in FIG. 1. The cylinder 24 is plugged at ends 25 and 26 and flow is through tube 27 past normally closed lips 27a and out tube 28. This permits flow in one direction only.

The check valves utilized for this purpose prevented any backflow even over 300 mmHg pressure but the pressure required to flow through these valves was below 5 mmHg. No bacterial contamination was noticed up to 74 hours of study utilizing a 0.22 micron filter with valves.

Considering the structure shown in FIGS. 1, 2 and 2A, it is apparent that all infusion connections of fresh dialysate solution are made ahead of the filter so that even if contamination does occur, the filter may reject it. It is therefore believed that the inclusion of a submicron filter on-line with fresh dialysate would be most beneficial in preventing peritoneal contamination.

Instead of the check valves and three-way valve shown in FIG. 1, the tube could be provided with tube clamps applied and removed to get the same results. The claims calling for check valves should be so understood.

Wherever in the specification and claims we have used the expression "dialysate from a flexible pressurized bag", it is intended to include "dialysate in a bottle with manual means to apply air pressure on the fluid in the bottle."

What is claimed is:

1. A filter connection for peritoneal dialysis comprising a sub-micron bacteria filter for removing sub-micron particles between about greater than 0.2 μm size, means to connect a pressurized source of fresh dialysate solution carried by the wearer to the upstream end of said filter, a tubular connection at the downstream end of said filter, a coacting first check valve in said tubular connection permitting flow only away from said filter, an outflow port communicating with said tubular connection downstream from said first check valve and independent of said filter, there being the equivalent of a second check valve in communication with said outflow port permitting flow only away from said port, and means for attaching to said tubular connection a catheter tube communicating with the peritoneum of a patient.

2. A filter connection for peritoneal dialysis as defined in claim 1 so arranged as to be mounted upon the body of a patient.

3. A filter connection for peritoneal dialysate as defined in claim 1 wherein said filter is lightweight and is of plastic and is flat in that its thickness is its minimum dimension.

* * * * *